United States Patent [19]

Kukes et al.

[11] Patent Number: 4,539,308
[45] Date of Patent: Sep. 3, 1985

[54] OLEFIN METATHESIS CATALYST

[75] Inventors: Simon G. Kukes; Robert L. Banks, both of Bartlesville, Okla.

[73] Assignee: Phillips Petroleum Company, Bartlesville, Okla.

[21] Appl. No.: 652,026

[22] Filed: Sep. 19, 1984

Related U.S. Application Data

[62] Division of Ser. No. 539,213, Oct. 5, 1983, Pat. No. 4,499,328.

[51] Int. Cl.$^3$ .................. B01J 21/08; B01J 23/30; B01J 23/50
[52] U.S. Cl. .................................................... 502/243
[58] Field of Search ................ 502/243, 254, 317, 347

[56] References Cited

U.S. PATENT DOCUMENTS

| | | | |
|---|---|---|---|
| 2,005,645 | 6/1935 | Bond et al. | 502/317 X |
| 3,200,063 | 8/1965 | Wilson | 502/317 X |
| 3,595,920 | 7/1971 | Ellis et al. | 260/683 D |
| 3,646,143 | 2/1972 | Ellis et al. | 260/683 D |
| 3,660,517 | 5/1972 | Reusser et al. | 585/646 |
| 3,764,635 | 10/1973 | Fattore et al. | 585/643 |
| 3,767,565 | 10/1973 | Banks | 585/643 |
| 3,775,509 | 3/1975 | Ellis et al. | 260/683 D |
| 3,785,956 | 10/1974 | Banks | 585/644 |
| 3,792,106 | 2/1974 | Regier | 585/644 |
| 3,792,107 | 2/1974 | Fattore et al. | 260/683 D |
| 3,872,180 | 3/1975 | Nakatomi et al. | 260/683 D |
| 4,287,378 | 9/1981 | Pannella | 585/643 |
| 4,368,345 | 1/1983 | Dickinson | 502/254 |
| 4,414,412 | 11/1983 | DeAlberti et al. | 502/317 X |

*Primary Examiner*—W. J. Shine
*Attorney, Agent, or Firm*—Howard D. Doescher

[57] ABSTRACT

Olefins are converted into other olefins having different numbers of carbon atoms by contact with a catalyst comprising silica containing tungsten oxide and a promoting amount of silver under conditions suitable for silver to promote the activity of tungsten oxide for the disproportionation reaction.

8 Claims, No Drawings

OLEFIN METATHESIS CATALYST

This is a divisional application of co-pending application Ser. No. 539,213, filed Oct. 5, 1983 now U.S. Pat. No. 4,499,328.

BACKGROUND OF THE INVENTION

This invention relates to the disproportionation (metathesis) of olefins. In accordance with one aspect, this invention relates to a catalyst suitable for use in the disproportionation of olefinic hydrocarbons. In accordance with another aspect, this invention relates to a process for the disproportionation of olefinic hydrocarbons. In accordance with a further aspect, this invention relates to a catalyst suitable for use in the disproportionation of olefins comprising tungsten oxide promoted with a small amount of silver. In accordance with a further aspect, this invention relates to a catalyst suitable for use in the disproportionation of olefins comprising silica and tungsten oxide promoted with silver oxide. In accordance with another aspect, this invention relates to a process for the disproportionation of olefinic hydrocarbons with a disproportionation catalyst as hereinbefore described under conditions of temperature and pressure which effect disproportionation of the feed.

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as a self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons.

Among the catalysts that have been developed for disproportionation are those comprising inorganic refractory materials, such as silica, containing a catalytic amount of tungsten oxide. The present invention is based upon the discovery of a way to improve the activity of such a catalyst.

Accordingly, an object of this invention is to provide a method for the conversion of olefins.

Another object of this invention is to provide a catalyst for the conversion of olefins.

Still another object of this invention is to provide a method for converting olefins to olefins having different numbers of carbon atoms than the feed hydrocarbons.

Still another object is to provide a method for improving the activity of a disproportionation catalyst for the conversion of olefins into olefins having different numbers of carbon atoms than the feed hydrocarbons.

Other aspects, objects and the several advantages of the invention will be apparent to one skilled in the art upon reading the disclosure including a detailed description of the invention and the appended claims.

SUMMARY OF INVENTION

In accordance with the present invention, a disproportionation (metathesis) catalyst comprising silica containing a catalytically effective amount of tungsten oxide is improved by contacting the catalyst with a promoting amount of sliver under conditions suitable for the silver to promote the activity of tungsten oxide.

Further, in accordance with a specific embodiment of the present invention, a disproportionation (metathesis) catalyst comprising silica containing a catalytically effective amount of tungsten oxide is improved by contacting the tungsten oxide catalyst with a promoting and activating amount of silver, such as silver nitrate, under conditions suitable for the silver compound to promote the activity of tungsten oxide.

Also according to the invention, a process is provided for the disproportionation of an olefinic hydrocarbon by contacting the same with a disproportionation catalyst as hereinbefore described under conditions of temperature and pressure which effect disproportionation of the feed.

DESCRIPTION OF PREFERRED EMBODIMENTS

The silica component of the catalyst can be any conventional catalyst-grade silica. Some examples are precipitated silica gel, microspheroidal silica, flame hydrolyzed silica, and silica aero-gels. These materials have appreciable surface area, usually in the range of 50–700 $m^2$ per g and can range from fine powders to coarse granules. These materials often contain small amounts of compounds of aluminum and of sodium in the order of a few tenths of a percent by weight and smaller. Trace amounts of other metals and such small amounts of these materials are acceptable.

The tungsten component of the catalyst of the invention can be incorporated into the silica support by any suitable method including, for example, impregnation, dry mixing, and coprecipitation. Tungsten oxide can be added directly or in the form of a tungsten compound that can be converted to the oxide by calcination.

Generally the finished catalyst contains from about 0.1 to about 30 percent by weight of the tungsten component calculated as the metal oxide and based on the total weight of the tungsten component and the silica component, although larger amounts can be used. In most instances a proper amount of the promoter is from about 1 to about 20 percent. Excellent results have been obtained with silica-based catalysts containing from about 2 to about 15 percent by weight of tungsten oxide.

The solid catalysts can be in any conventional catalytic shape or size, depending upon the type of conversion in which it is to be utilized. For example, in fixed bed catalyst systems, the solid composite can be in the form of spheres, pellets, extrudates, agglomerates, and the like. In slurry catalyst systems, the solid can be in the form of relatively small particles or in the form of a powder.

To be effective in the present catalyst system, the above-described component of the catalysts is activated by calcination at elevated temperatures, generally in flowing air. The activation of the catalysts is accomplished at a temperature of from about 300° to about 800° C. for a period of several minutes to several hours or longer. When the solid component of the catalyst system is tungsten oxide on silica, a convenient and economical treatment is in the temperature range of 400°–700° C. for 0.5 to 20 hours or longer. In some cases the activation using an oxygen-containing gas can be followed by treatment, also at elevated temperatures, with other treating gases such as carbon monoxide, hydrogen, and the like.

The silver promoter of the invention can be combined with the thus prepared catalyst in any suitable manner. The silver promoter can be incorporated into the tungsten oxide catalyst as silver oxide or as a silver compound convertible to the oxide by calcination. For example, the catalyst is impregnated with a liquid diluent containing the promoting agent. After impregnation the catalyst is then heated in an inert atmosphere, such as nitrogen or argon, to remove the liquid diluent. The temperature employed in removing the diluent and drying can vary widely; however, temperatures in the range of about 300° C. to about 800° C. are currently preferred. If desired, the promoting agent can be applied to the catalyst in a reaction zone by spraying or otherwise contacting the catalyst. It is also contemplated that the promoting agent can be introduced along with olefin feed for contacting with the catalyst.

Thus, in accordance with the invention, calcined, tungsten oxide-silica catalysts are treated with an effective catalytically promoting amount of silver such as silver oxide or a silver compound convertible to the oxide and heated and calcined in an oxygen-containing atmosphere, such as air, under conditions to form a promoted catalyst. Calcination conditions that can be used are the same as described above with respect to activating the tungsten oxide.

Suitable silver compounds convertible to silver oxide upon calcination that can be used in addition to silver oxide ($Ag_2O$) and silver in the preparation of the invention catalyst include silver nitrate ($AgNO_3$), silver acetate ($AgC_2H_3O_2$), silver benzoate ($AgC_7H_5O_2$), silver bromate ($AgBrO_3$), silver carbonate ($Ag_2CO_3$), silver chlorate ($AgClO_3$), silver chloride ($AgCl$), silver chlorite ($AgClO_2$), silver citrate ($Ag_3C_6H_5O_7$), silver cyanate ($AgOCN$), silver fluoride ($AgF.H_2O$), silver sulfate ($Ag_2SO_4$), silver tartrate ($Ag_2C_4H_4O_6$), silver tungstate ($Ag_2WO_4$), and the like, and mixtures thereof. Silver nitrate is presently preferred.

The optimum amounts of catalyst promoting or treating agent employed can readily be determined by routine experimentation. Generally, the promoting agent should be used in an amount in the range of about 0.01 to about 10 weight percent, calculated as the metal, preferably about 0.1 to about 5 weight percent, more preferably about 0.5 to about 2 weight percent, based on the total weight of tungsten oxide and silica prior to the addition of the promoting silver agent.

The promoted catalyst can be used in disproportionation reactions in a conventional manner. The reaction temperature can vary depending upon the catalyst and feed(s) employed, but will be sufficient to effect disproportionation. Typically, the disproportionation is carried out at a temperature in the range of about 20° to about 600° C.

The disproportionation reaction can be carried out by contacting the olefins to be disproportionated with the catalyst in the liquid phase or the gas phase, depending on structure and molecular weight of the olefins, temperature and pressure.

Olefins applicable for use in the process of the invention are nontertiary, nonconjugated acyclic mono- and polyenes having at least 3 carbon atoms per molecule including cycloalkyl, cycloalkenyl, and aryl derivatives thereof; cyclic and polycyclic mono- and polyenes having at least 4 carbon atoms per molecule including alkyl and aryl derivatives thereof; mixtures of the above olefins; and mixtures of ethylene and the above olefins. Many useful reactions are accomplished with such acyclic olefins having 3–30 carbon atoms per molecule and with such cyclic olefins having 4–30 carbon atoms per molecule. Nontertiary olefins are those olefins wherein each carbon atom, which is attached to another carbon atom by means of a double bond, is also attached to at least one hydrogen atom. Mono-olefins are preferred.

Some specific examples of acyclic olefins suitable for reactions of this invention include propylene, 1-butene, 2-butene, 1-pentene, 2-pentene, 1-hexene, 1,4-hexadiene, 2-heptene, 1-octene, 2,5-octadiene, 2-nonene, 1-dodecene, 2-tetradecene, 1-hexadecene, 1-phenylbutene-2, 4-octene, 3-eicosene, 3-hexene, 1,4-pentadiene, 1,4,7-dodecatriene, 2-methyl-4-octene, 4-vinylcyclohexane, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures thereof.

Some specific examples of cyclic olefins suitable for the reactions of this invention are cyclobutene, cyclopencene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethylcyclooctadiene-1,4, and the like, and mixtures thereof.

The pressure during the disproportionation reaction may vary between wide limits. Pressures between 0.1 and 500 atm. are suitable; preferred pressures are between 0.5 and 250 atm.

If the reaction is carried out in the liquid phase, solvents or diluents for the reactants may be used. Aliphatic saturated hydrocarbons (e.g., pentane, hexane, cyclohexane, dodecane) and aromatic hydrocarbons such as benzene and toluene are suitable. If the reaction is carried out in the gaseous phase, diluents such as aliphatic hydrocarbons (e.g., methane, ethane) and/or inert gases (e.g., nitrogen, argon) can be present. Preferably the disproportionation reaction is effected in the substantial absence of reactive materials such as water and oxygen.

The length of time during which the olefinically unsaturated compounds to be disproportionated are contacted with the catalyst depends upon several factors such as the activity of the catalyst, temperature, pressure, and structure of the olefinically unsaturated compound to be disproportionated. Contact time can conveniently vary between 1 second and 24 hours, although longer and shorter contact times may be used. The contact time needed to obtain a reasonable yield of disproportionated products depends on the factors mentioned above.

The process of the invention is effected batchwise or continuously, with fixed catalyst beds, slurried catalysts, fluidized beds or by using any other conventional contacting technique. The solid disproportionation catalysts are employed in any appropriate form, for example, as powders, flakes, pellets, spheres or extrudates.

The olefinic products of the invention, for the most part, have established utility as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form Nylons which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

In each example the tungsten oxide content of the catalyst was 6 weight percent based on the total weight of tungsten oxide and silica. The catalysts were prepared by impregnating high surface area silica with 0.0727 gram of ammonium metatungstate $((NH_4)_2W_4O_{13}\cdot 8H_2O)$ per gram of silica. The impregnation was accomplished by treating the silica with an aqueous solution of the ammonium metatungstate. The impregnated silica was dried and calcined in air at 500° C. to convert the metatungstate to the oxide. A −20+40 mesh sieve fraction was obtained for use as described below.

The supported tungsten oxide was then impregnated with aqueous solutions of silver nitrate. After drying to remove water, the catalysts were calcined in an air flow at about 600° C. to convert the nitrate to the desired oxide.

All runs were made by passing a propylene feed through a vertical tubular quartz reactor (1 cm in diameter and 25 cm in length) positioned in a temperature-controlled electric furnace. In each run the reactor contained a bed of the designated catalyst. A thermocouple was positioned in the catalyst bed to monitor reaction temperature. Prior to each run the catalyst was activated by heating at 600° C. in flowing nitrogen for 0.5 hours. Regeneration, when indicated, was accomplished with flowing air at 600° C. for one hour, followed by a nitrogen flush at 600° C. The propylene feed was of a polymerization grade as sold by Phillips Petroleum Company of Bartlesville, Okla. The propylene feed was pretreated with activated Alcoa H151 alumina and activated magnesia prior to metathesis. The feed was passed downwardly through the vertically oriented tubular reactor. Reaction product analyses were made by gas-liquid chromatography (GLC) employing a Hewlett-Packard model 5880A chromatograph having a ⅛ inch by 20 ft. column packed with 19% BMEE +1% squalene on 60/80 Chrom P. Analysis was carried out isothermally at a temperature of 30° C. with a helium carrier gas flow rate of about 20 mL/min.

EXAMPLE I

Several control runs were carried out using the 6% $WO_3$ on silica catalyst prepared as described above. Catalyst (1.5g) was placed in the tubular reactor, heated to 540° C. under an air flow of 150 mL/min. and maintained under those conditions for 30 minutes. Air flow was then replaced with a stream of nitrogen at 150 mL/min. and the catalyst bed heated to 600° C. and maintained at that temperature for 30 minutes. After 30 minutes at 600° C., nitrogen flow was maintained while the catalyst bed was allowed to cool to the desired reaction temperature. Propylene feed was introduced at about 130 mL/min. Results at three different reaction temperatures are given below in Table I.

TABLE I

| Run | Temperature, °C. | Reaction time, min | Propylene Conversion, % | % 1-Butene of total butenes |
|---|---|---|---|---|
| 1 | 425 | 50 | 12.6 | 1.3 |
|   |     | 91 | 13.2 | 1.2 |
| 2 | 450 | 47 | 22.5 | 2.9 |
|   |     | 89 | 23.6 | 2.8 |
| 3 | 500 | 45 | 44.4 | 6.2 |
|   |     | 85 | 45.2 | 6.6 |

These results indicate that $WO_3\cdot SiO_2$ catalyst is effective for conversion of propylene to butenes. Increased propylene conversion and greater isomerization to 1-butene is observed as temperature increases.

EXAMPLE II

Several invention catalysts were prepared by impregnating the 6% $WO_3$ on silica catalyst with aqueous solutions of silver nitrate. The aqueous solutions were warmed as necessary to cause dissolution of the desired amount of $AgNO_3$. The aqueous $AgNO_3$ solutions were added to $WO_3\cdot SiO_2$ catalyst prepared as described above, oven dried, then calcined at 500°–600° C. in air for 2–4 hours prior to placing in the reactor. Silver loading is reported as weight % silver metal, based on the weight of $WO_3$-$SiO_2$ treated.

TABLE II

| Catalyst | $AgNO_3$, g | $WO_3.SiO_2$, g | $H_2O$, mL | Ag loading |
|---|---|---|---|---|
| A | 0.02 | 5.0 | 15 | 0.25 |
| B | 0.05 | 5.5 | 12 | 0.5 |
| C | 0.20 | 11.4 | 17 | 1.1 |
| D | 0.09 | 5.0 | 6.5 | 1.1 |
| E | 0.80 | 5.0 | 10.0 | 10.0 |

EXAMPLE III

Several reactions were carried out using the invention catalysts prepared as described above. Catalyst activation was carried out as described in Example I. Once catalyst activation was complete and the reactor had cooled to the desired reaction temperature, propylene feed was introduced at the rate of about 130 mL/min. Reaction parameters and results are summarized in Table III.

TABLE III

| Catalyst | Temperature, °C. | Reaction time, min | Propylene Conversion % | % 1-Butene of total butenes |
|---|---|---|---|---|
| B | 450 | 65 | 26.4 | 24.5 |
| C | 450 | 55 | 28.9 | 25.4 |
| D | 425 | 50 | 14.4 | 4.6 |
|   |     | 112 | 15.3 | 4.3 |
| E | 500 | 65 | 36.4 | 25.1 |
|   |     | 105 | 38.3 | 25.1 |

These results demonstrate the enhanced propylene conversion and increased formation of 1-butenes which can be achieved with the inventive silver oxide promoted $WO_3\cdot SiO_2$ catalyst.

EXAMPLE IV

A control run was carried out using 2.8 g of Calsicat ® pure MgO on top of (upstream) 1.5 g of 6%

$WO_3 \cdot SiO_2$ catalyst (equal volumes). Catalyst was activated by heating to 600° C. in an air flow of 150 mL/min for 1 hour, then purged with nitrogen for 15 minutes at 150 mL/min, then the reactor was cooled to 400° C. Carbon monoxide at 50 mL/min was passed over the cooled (400° C.) catalyst for 15 minutes, followed by a 5 minute purge with $N_2$ at 150 mL/min. Propylene was then introduced at 150 mL/min at a reaction temperature of 400° C. Propylene conversion after about 1 hour on stream was 44.3% with 1-butene representing 1.6% of the total butene fraction.

EXAMPLE V

The procedure described in Example IV was repeated, except 1.6 g of invention catalyst A and 2.9 g of Calsicat ® pure MgO (equal volumes) were employed. Catalyst activation was carried out as described above and a reaction temperature of 400° C. and propylene flow rate of 150 mL/min were similarly employed. Propylene conversion after about one hour on stream was 44.4% with a 2.6% 1-butene content of the total butene fraction.

This example demonstrates that silver oxide promoted $WO_3 \cdot SiO_2$ catalyst gives improved isomerization activity compared to non-promoted catalyst (compare Example IV) in the presence of an additional reaction promoter such as MgO.

What is claimed is:

1. A catalytic composition suitable for the disproportionation of olefins consisting silica of and tungsten oxide promoted with an effective promoting amount of silver oxide.

2. A composition according to claim 1 wherein the amount of pungsten oxide is in the range of about 0.1 to about 30 percent by weight of the combined weights of tungsten oxide and silica prior to the addition of silver.

3. A catalytic composition suitable for the disproportionation of olefins consisting of calcined silica support and tungsten oxide promoted with about 0.01 to about 10 weight percent silver, calculated as the metal, based on the tungsten oxide-silica material combination.

4. A process for preparing a disproportionation catalyst consisting of admixing a catalytically effective amount of tungsten oxide and silica support with a promoting amount of at least one of silver, silver oxide, and silver compounds convertible to silver oxide, and subjecting same to conditions suitable for silver to promote the activity of tungsten oxide for the disproportionation of olefins.

5. A process according to claim 4 wherein a sliver compound is admixed in solution with the tungsten oxide-silica combination and the resulting composition is dried and calcined at a temperature in the range of about 300° C. to about 800° C.

6. A process according to claim 4 wherein said catalytic amount of tungsten oxide is in the range of about 0.1 to about 30 percent by weight of the combined weights of tungsten oxide and silica prior to the addition of silver.

7. A process according to claim 4 wherein sliver is employed in an amount in the range of about 0.01 to about 10 weight percent, calculate as the metal, based on the weight of the tungsten oxide-silica combination prior to the addition of silver or silver compound.

8. A process according to claim 6 wherein silver nitrate is admixed with a calcined tungsten oxide-silica catalyst and dried and calcined at a temperature in the range of about 300° C. to about 800° C.

* * * * *

UNITED STATES PATENT AND TRADEMARK OFFICE
CERTIFICATE OF CORRECTION

PATENT NO. : 4,539,308
DATED : September 3, 1985
INVENTOR(S) : SIMON G. KUKES et al It is certified that error appears in the above-identified patent and that said Letters Patent is hereby corrected as shown below:

Col. 7, claim 1, line 31, "silica of" should read "of silica".

Col. 7, claim 2, line 35, "pungsten" should be ---tungsten---.

Col. 8, claim 7, line 28, "calculate" should be ---calculated---.

Signed and Sealed this

Twenty-third Day of September 1986

[SEAL]

Attest:

DONALD J. QUIGG

Attesting Officer

Commissioner of Patents and Trademarks